US00PP24370P2

(12) United States Plant Patent
Ikeda

(10) Patent No.: US PP24,370 P2
(45) Date of Patent: Apr. 1, 2014

(54) ***PETUNIA* PLANT NAMED 'SUNPAPUHU'**

(50) Latin Name: *Petunia×hybrida*
Varietal Denomination: Sunpapuhu

(75) Inventor: Yukihiro Ikeda, Hyogo (JP)

(73) Assignee: Suntory Flowers Ltd., Tokyo (JP)

( * ) Notice: Subject to any disclaimer, the term of this patent is extended or adjusted under 35 U.S.C. 154(b) by 85 days.

(21) Appl. No.: 13/506,816

(22) Filed: May 17, 2012

(51) Int. Cl.
*A01H 5/00* (2006.01)

(52) U.S. Cl.
USPC ..... Plt./356.22

(58) Field of Classification Search
USPC ..... Plt./356.22
See application file for complete search history.

(56) References Cited

PUBLICATIONS

UPOV PLUTO 201303 QZ Citation for 'Sunpapuhu' Aug. 15, 2011.*
UPOV PLUTO 201303 CA Citation for 'Sunpapuhu' Apr. 19, 2013.*

* cited by examiner

*Primary Examiner* — Wendy C Haas
(74) *Attorney, Agent, or Firm* — C. A. Whealy

(57) ABSTRACT

A new and distinct cultivar of *Petunia* plant named 'Sunpapuhu', characterized by its mounding and trailing plant habit; vigorous growth habit; freely branching habit; green and pale yellow variegated leaves; long flowering period; medium-sized red purple-colored flowers with violet-colored throats; and good garden performance.

1 Drawing Sheet

Botanical designation: *Petunia×hybrida*.
Cultivar denomination: 'SUNPAPUHU'.

BACKGROUND OF THE INVENTION

The present invention relates to a new and distinct cultivar of *Petunia* plant, botanically known as *Petunia×hybrida* and hereinafter referred to by the name 'Sunpapuhu'.

The new *Petunia* plant is a product of a planned breeding program conducted by the Inventor in Akashi, Hyogo, Japan. The objective of the breeding program is to create new *Petunia* plants with trailing habit and attractive leaf and flower coloration.

The new *Petunia* plant is a naturally-occurring branch mutation of a proprietary selection of *Petunia×hybrida* identified as code name Purple-M1, not patented. The new *Petunia* plant was discovered and selected by the Inventor on a single flowering plant from within a population of plants of the parent selection in a controlled environment in Akashi, Hyogo, Japan in August, 2006.

Asexual reproduction of the new *Petunia* plant by terminal cuttings in a controlled environment in Akashi, Hyogo, Japan since August, 2006 has shown that the unique features of this new *Petunia* plant are stable and reproduced true to type in successive generations.

SUMMARY OF THE INVENTION

Plants of the new *Petunia* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunpapuhu'. These characteristics in combination distinguish 'Sunpapuhu' as a new and distinct *Petunia* plant:

1. Mounding and trailing plant habit.
2. Vigorous growth habit.
3. Freely branching habit.
4. Green and pale yellow variegated leaves.
5. Long flowering period.
6. Medium-sized red purple-colored flowers with violet-colored throats.
7. Good garden performance.

Plants of the new *Petunia* can be compared to plants of the parent selection. Plants of the new *Petunia* differ primarily from plants of the parent selection in leaf color as plants of the parent selection do not have variegated leaves. In addition, petals of the new *Petunia* have acute apices whereas petals of plants of the parent selection have rounded apices.

Plants of the new *Petunia* can also be compared to plants of the *Petunia* 'Sunripami', not patented. In side-by-side comparisons conducted in Higashiomi, Shiga, Japan, plants of the new *Petunia* and 'Sunripami' differed primarily in the following characteristics:

1. Plants of the new *Petunia* were smaller than plants of 'Sunripami'.
2. Leaves of plants of the new *Petunia* were elliptic in shape whereas leaves of plants of 'Sunripami' were more lanceolate in shape.
3. Leaves of plants of the new *Petunia* were variegated whereas leaves of plants of 'Sunripami' were not variegated.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunpapuhu' grown in a container.

The photograph at the bottom of the sheet is a close-up view of a typical flowering plant of 'Sunpapuhu'.

DETAILED BOTANICAL DESCRIPTION

The aforementioned photographs and following observations, measurements and values describe plants grown during the late spring in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Petunia×hybrida* 'Sunpapuhu'.

Parentage: Naturally-occurring branch mutation of a proprietary selection of *Petunia×hybrida* identified as code name Purple M1, not patented.

Propagation:

*Type.*—By terminal cuttings.

*Time to initiate roots.*—About one week at temperatures of 15° C. to 20° C.

*Time to produce a rooted young plant.*—About three weeks at temperatures of 15° C. to 20° C.

*Root description.*—Fibrous; white in color.

*Rooting habit.*—Freely branching.

Plant description:

*Plant and growth habit.*—Mounding and trailing plant habit; moderately branching habit with numerous lateral branches developing per plant; pinching enhances lateral branch development; vigorous growth habit.

*Plant height.*—About 13.8 cm.

*Plant diameter.*—About 51.2 cm.

Lateral branch description:

*Length.*—About 26 cm.

*Diameter.*—About 2.2 mm.

*Internode length.*—About 1.7 cm.

*Strength.*—Strong, flexible.

*Aspect.*—Decumbent.

*Texture.*—Densely pubescent.

*Color.*—Close to 138B.

Foliage description:

*Arrangement.*—Alternate, simple.

*Length.*—About 2 cm.

*Width.*—About 4.2 cm.

*Shape.*—Elliptic.

*Apex.*—Broadly acute.

*Base.*—Attenuate.

*Margin.*—Entire, undulate.

*Texture, upper and lower surfaces.*—Pubescent.

*Venation pattern.*—Pinnate.

*Color.*—Developing and fully developed leaves, upper surface: Variegated; center, random sectors close to 137C; towards the margins, random sectors close to 3D; venation, close to 138B. Developing and fully developed leaves, lower surface: Variegated; center, random sectors close to 137D; towards the margins, random sectors close to 154C; venation, close to 138B.

*Petioles.*—Length: About 5.1 mm. Diameter: About 1.6 mm. Texture, upper and lower surfaces: Pubescent. Color, upper and lower surfaces: Close to 138B.

Flower description:

*Flower arrangement and habit.*—Single salverform flowers arising from upper leaf axils; freely flowering habit with usually about 63 flowers developing per plant; flowers face upright to outwardly.

*Fragrance.*—Fragrant, pleasant.

*Natural flowering season.*—Early flowering habit, plants of the new *Petunia* initiate and develop flowers about three to four weeks after planting; long flowering period, flowering commences naturally during the spring and plants flower continuously throughout the summer into the late autumn in Japan.

*Flower longevity.*—Individual flowers last about seven to ten days on the plant; flowers not persistent.

*Flower diameter.*—About 4.6 cm.

*Flower length (depth).*—About 3.4 cm.

*Throat diameter.*—About 1 cm.

*Tube diameter, base.*—About 2.1 mm.

*Tube length.*—About 1.9 cm.

*Flower buds.*—Shape: Cylindrical. Length: About 2.75 cm. Diameter: About 4.7 mm. Color: Close to 79C.

*Corolla.*—Arrangement: Five petals fused at the base and opening into a flared trumpet. Petal length from throat: About 2.1 cm. Petal width: About 1.8 cm. Petal shape: Spatulate. Petal apex: Acute. Petal margin: Entire. Petal texture, upper and lower surfaces: Smooth, glabrous. Throat texture: Smooth, glabrous. Tube texture: Pubescent. Color: Petal, when opening, upper surface: Deeper in color than N74A. Petal, when opening, lower surface: Close to N80B. Petal, fully opened, upper surface: Close to N74A; venation, close to N74A; color does not change with development. Petal, fully opened, lower surface: Close to N80B; venation, close to N80B. Throat: Close to N87A; venation, close to N87A. Tube: Close to N80A; venation, close to 79A.

*Calyx.*—Arrangement: One star-shaped calyx tube with five sepals fused at the base per flower. Sepal length: About 1.1 cm. Sepal width: About 2.8 mm. Sepal shape: Narrowly elliptic. Sepal apex: Obtuse. Sepal margin: Entire. Sepal texture, upper and lower surfaces: Pubescent. Color: Developing and fully developed sepals, upper surface: Variegated, random sectors of close to 3D and 137C. Developing and fully developed sepals, lower surface: Variegated, random sectors of close to 154C and 137D.

*Peduncles.*—Length: About 2 cm. Diameter: About 0.8 mm. Strength: Strong. Texture: Pubescent. Color: Close to 138B.

*Reproductive organs.*—Stamens: Quantity per flower: Five. Stamen length: About 1 cm to 1.6 cm. Anther shape: Ellipsoidal. Anther size: About 1.6 mm by 2.1 mm. Anther color: Close to 91A. Pollen amount: Moderate. Pollen color: Close to 97B. Pistils: Quantity per flower: One. Pistil length: About 1.5 cm. Style color: Close to 144D. Stigma shape: Transversely ellipsoidal. Stigma color: Close to 144B. Ovary color: Close to 144B. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunpapuhu' as illustrated and described.

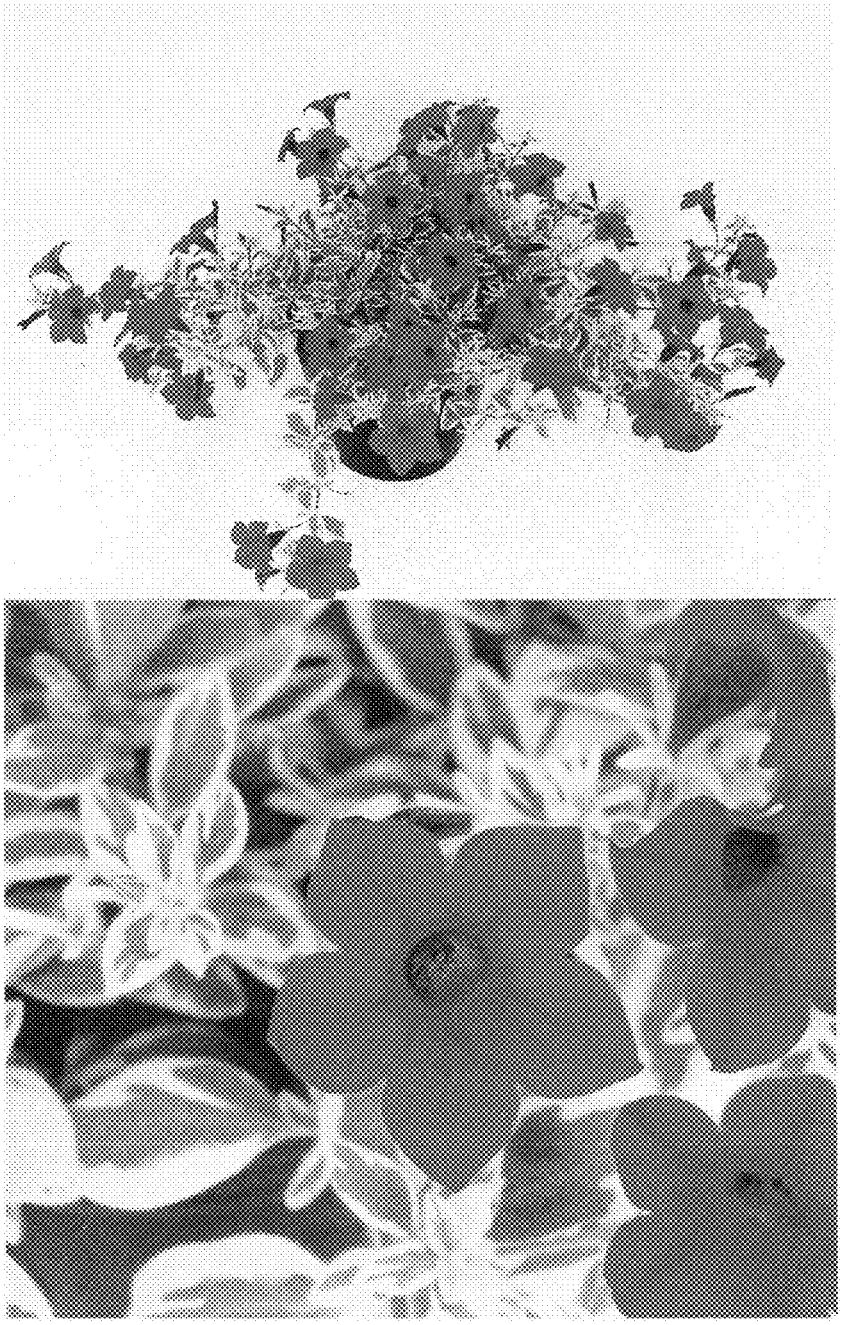

* * * * *